(12) United States Patent
Root

(10) Patent No.: US 10,751,503 B2
(45) Date of Patent: Aug. 25, 2020

(54) BONE CONDUCTION BODY SUPPORT SYSTEM

(71) Applicant: Philip Root, Boca Raton, FL (US)

(72) Inventor: Philip Root, Boca Raton, FL (US)

(*) Notice: Subject to any disclaimer, the term of this patent is extended or adjusted under 35 U.S.C. 154(b) by 270 days.

(21) Appl. No.: 15/871,550

(22) Filed: Mar. 2, 2018

(65) Prior Publication Data

US 2019/0269880 A1 Sep. 5, 2019

(51) Int. Cl.
*A61M 21/02* (2006.01)
*A47G 9/10* (2006.01)
*A47C 7/72* (2006.01)
*A47C 21/00* (2006.01)
*A61M 21/00* (2006.01)
*A47G 9/00* (2006.01)
*A47G 9/02* (2006.01)
*A47C 31/10* (2006.01)
*A47C 31/11* (2006.01)

(52) U.S. Cl.
CPC .......... *A61M 21/02* (2013.01); *A47C 7/72* (2013.01); *A47C 21/003* (2013.01); *A47G 9/1045* (2013.01); *A47C 31/10* (2013.01); *A47C 31/11* (2013.01); *A47G 9/0253* (2013.01); *A47G 2009/006* (2013.01); *A61M 2021/0027* (2013.01); *A61M 2205/3584* (2013.01); *A61M 2205/8206* (2013.01); *A61M 2205/8262* (2013.01); *H04R 2400/03* (2013.01)

(58) Field of Classification Search
CPC .......... A61M 21/02; A61M 2205/8206; A61M 2205/8262; A61M 2205/3584; A61M 2021/0027; A47C 21/003; A47C 7/72; A47C 31/11; A47C 31/10; A47G 9/1045; A47G 9/0253; A47G 2009/006; H04R 2400/03

See application file for complete search history.

(56) References Cited

U.S. PATENT DOCUMENTS

| | | | |
|---|---|---|---|
| 2007/0053530 A1* | 3/2007 | Ochiai | H04R 5/023 381/151 |
| 2013/0043988 A1* | 2/2013 | Bruno | A47G 9/0253 340/407.1 |
| 2013/0090520 A1* | 4/2013 | Redfield | A61M 21/00 600/28 |
| 2017/0013979 A1* | 1/2017 | Kim | A47G 9/1045 |
| 2017/0143254 A1* | 5/2017 | Bell | A47G 9/10 |
| 2018/0063612 A1* | 3/2018 | Fuchs | H04R 5/023 |

FOREIGN PATENT DOCUMENTS

CN 104510243 A * 4/2015

* cited by examiner

*Primary Examiner* — Kaylee R Wilson
(74) *Attorney, Agent, or Firm* — The Rapacke Law Group PA

(57) ABSTRACT

Embodiments described herein provide for a bone conduction system configured as a pillow, bed cushion, seat or similar body support device. The bone conduction system comprises a plurality of transducers positioned about the pillow, bed cushion, seat or similar body support. When ergonomically positioned on the user's skull, the plurality of transducers transmit sound waves to the inner ear.

19 Claims, 8 Drawing Sheets

BONE CONDUCTION BODY SUPPORT SYSTEM

FIELD

The present invention relates to devices for providing vestibular and somatosensory stimulation utilizing bone conduction technologies.

BACKGROUND

The human body can sense sound by air conduction as well as bone conduction. While air conduction is how we typically converse and hear our surroundings, bone conduction can also stimulate the vestibular and somatosensory systems as sound vibration is transmitted through the body's skeletal framework.

Stimulating these sensory systems using bone conduction has been proven to result in a variety of benefits including the promotion of neurological development, relaxation and stabilization of the body. Auditory devices have also been used to help treat and/or prevent ADHD, autism, Asperger's, and sensory processing disorder among others. These auditory devices have consisted of air conduction headphones as well as bone conduction devices attached to the user's headphones. While these have been effective, these devices may be uncomfortable. Further, it has been shown that vestibular stimulation in-utero provides similar benefits to the fetus, for which prior art devices are not practical.

It can be seen that advancements in the field of bone conduction devices is needed in light of the limitations found in the prior art. It is an object of the present invention to provide for a device to stimulate vestibular and somatosensory systems for use in adults, children, infants, and premature infants alike. One such advancement is provided herein.

SUMMARY OF THE INVENTION

Embodiments described herein provide for a bone conduction device preferentially configured as a pillow or other body support systems. The embodiments provided disclose a device comprised of a flexible cover having an exterior surface defining an interior cavity. The cover has a batting disposed therein to support a user's head or neck region wherein a plurality of bone conduction transducers is in proximate contact with the exterior surface. The bone conduction transducers are disposed between the flexible cover and the batting, wherein each of the plurality of bone conduction transducers are configured to transmit sounds waves to stimulate a user through bone conduction. Further, a sound source is in communication with a wireless transmitter, wherein the wireless transmitter is electrically connected to and transmitting signals to the plurality of bone conduction transducers. One or more USB ports electrically connected to a power source, wherein the power source is configured to receive, store, and transmit power to the plurality of bone conduction transducers.

A method of stimulating a user using bone conduction is disclosed including the steps of disposing a bone conduction system within a flexible cover. Next, an audio signal is transmitted to the bone conduction system utilizing an audio source. The signal is received by a wireless receiver and transduced to stimulate the vestibular/somatosensory system of a user.

In another embodiment, the bone conduction system includes a control panel disposed on the exterior surface permitting the user to manage the audio levels, ON/OFF functions, and other controls from the exterior of the cover.

In another embodiment, each bone conduction transducer is positioned proximate to the head of the user. Preferentially, each bone conduction transducer is positioned to sufficiently contact each temporal bone of the user.

For appropriate stimulation to the user each bone conduction transducer may be configured to emit sound vibrations having a frequency range between 50 and 4,000 Hz.

Other aspects, advantages, and novel features of the embodiments will become apparent from the following detailed description in conjunction with the figures.

BRIEF DESCRIPTION OF THE DRAWINGS

A more complete understanding of the embodiments, and the attendant advantages and features thereof, will be more readily understood by references to the following detailed description when considered in conjunction with the accompanying drawings wherein.

DETAILED DESCRIPTION

The specific details of the single embodiment or variety of embodiments described herein are set forth in this application. Any specific details of the embodiments are used for demonstration purposes only and no unnecessary limitation or inferences are to be understood therefrom.

The present embodiments provide for a body support structure having integrated bone conductors and associated electrical components in communication thereto. Each bone conductor is comprised of at least one transducer configured to transmit stimulation to the skeletal structure of the user. Each bone conductor is embedded within a bodily support device, and depending on its overall size, may be placed underneath, on top of, or around a user who is receiving the auditory stimulation. The body support device may be constructed from a few inches square or any larger size. Each transducer is applied to permit the conduction of sound waves to any part of the user's skeletal framework. The bodily support device having embedded transducers may also be suitably applied to conduct sound to a fetus (secondary user).

Figure 1:
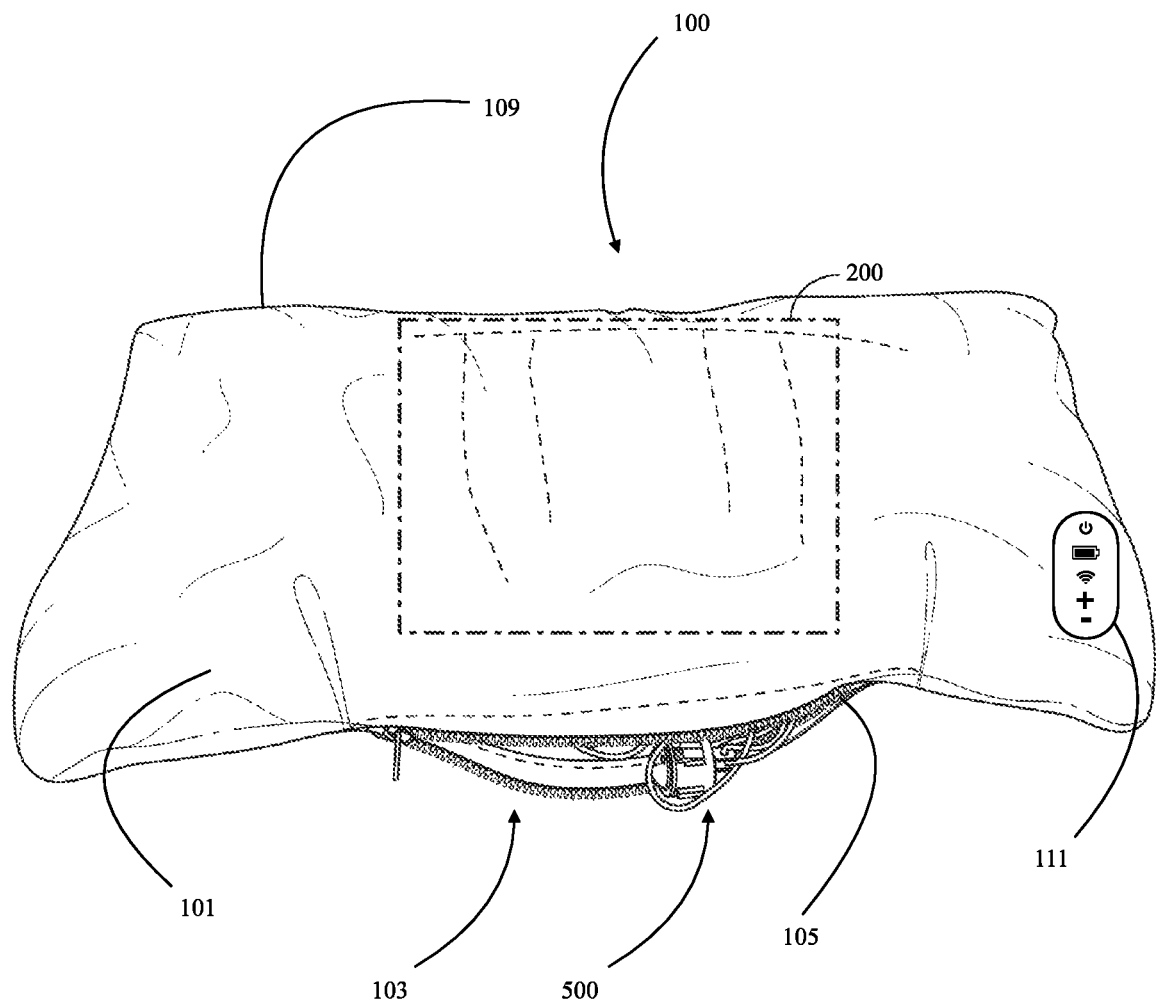
FIG. 1 illustrates a perspective view of the body support device having integrated bone conduction assembly, according to an embodiment of the present invention.

Referencing FIG. 1, the bone conduction system 100 is illustrated having integrated bone conduction transducers and electric assembly 500 connected thereto. The electrical assembly 500 is disposed within the interior of the bone conduction system 100 which is illustrated in the instant embodiment as a pillow. The bone conduction system 100 has a flexible exterior 101 and perimeter 109 defining an interior cavity 103. The interior cavity 103 may be selectively opened or closed using a zipper 105 or similar means of textile connection such as a hook and loop system, adhesive, or button system.

Further illustrated in FIG. 1 is a control panel 111 positioned on the exterior surface 101 of the system 100. The control panel 111 is comprised of a ON/OFF button, volume controls, a battery indicator and a signal indicator as well as other controls known in the arts.

Figure 2:
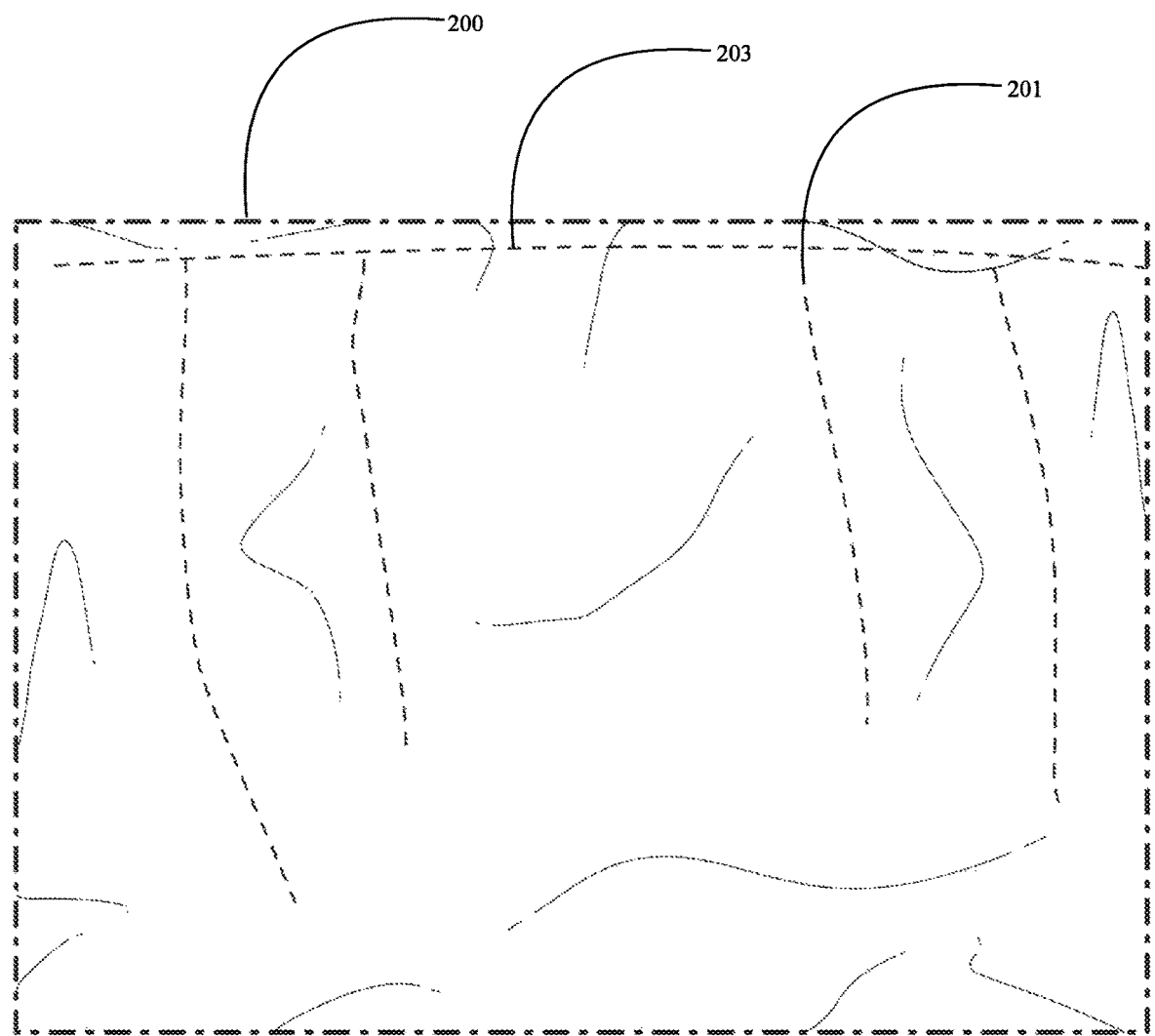
FIG. 2 illustrates a cutaway view of the exterior surface of the secondary pocket region, according to an embodiment of the present invention.

In another embodiment, the exterior may have a stitched region 200 defining a perimeter of a secondary pocket disposed within the interior cavity. A detailed view of the stitched region 200 is illustrated in FIG. 2. One skilled in the arts may appreciate that external stitching 201 may not be necessary as solely internal means for secondary pocket attachment such as adhesives may be utilized. When viewed from the exterior surface or interior surface, the secondary pocket has at least one opening permitting the ingress and egress of the electrical components 500. Stitching 201, 203 or other means of textile adhesion may define the perimeter of the secondary pocket such that the electrical components 500 may be retained therein.

Figure 3:
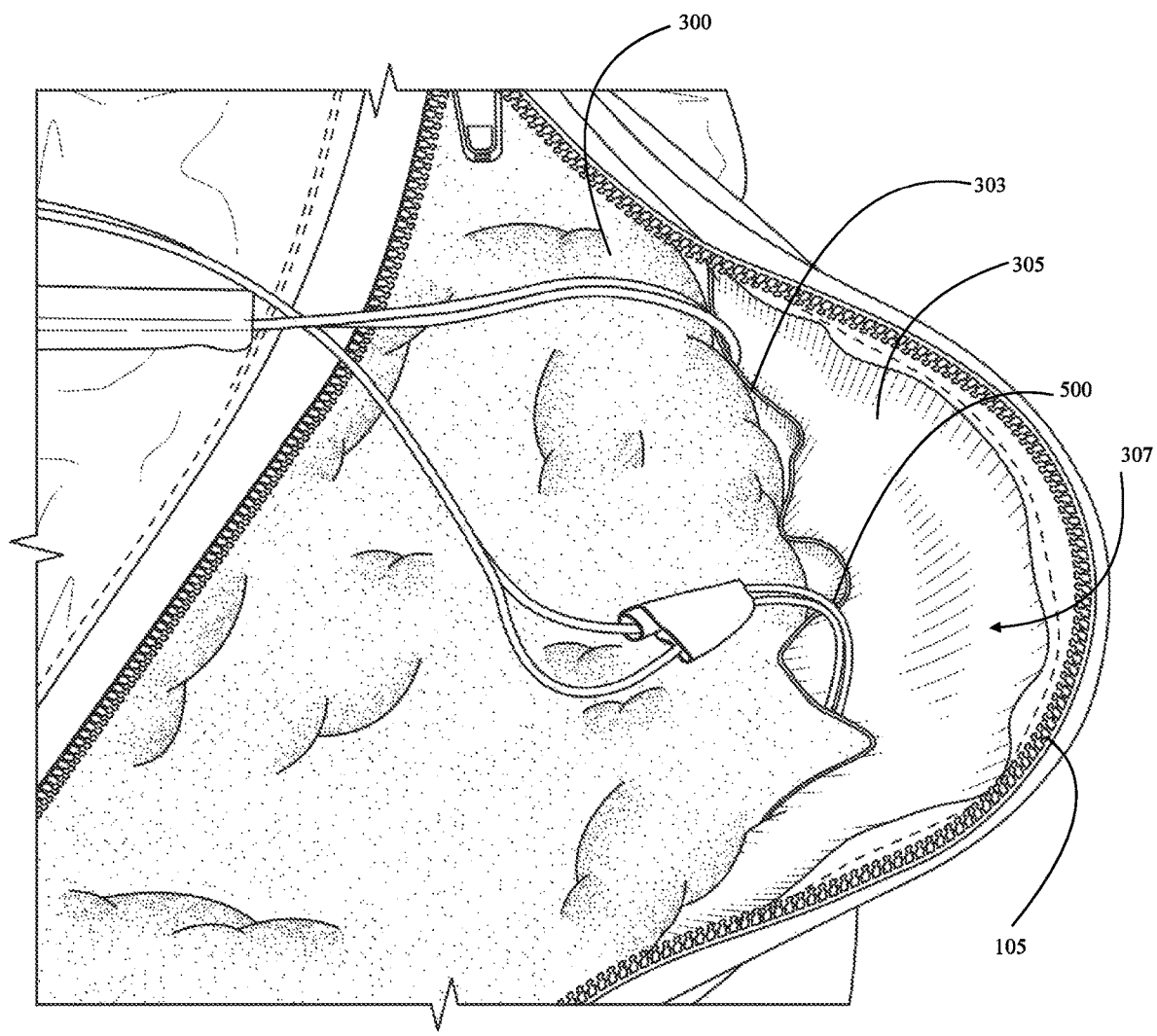
FIG. 3 illustrates a detailed view of the interior cavity of the device, batting, relative positioning of electronic components and closure means, according to an embodiment of the present invention.
Figure 4:
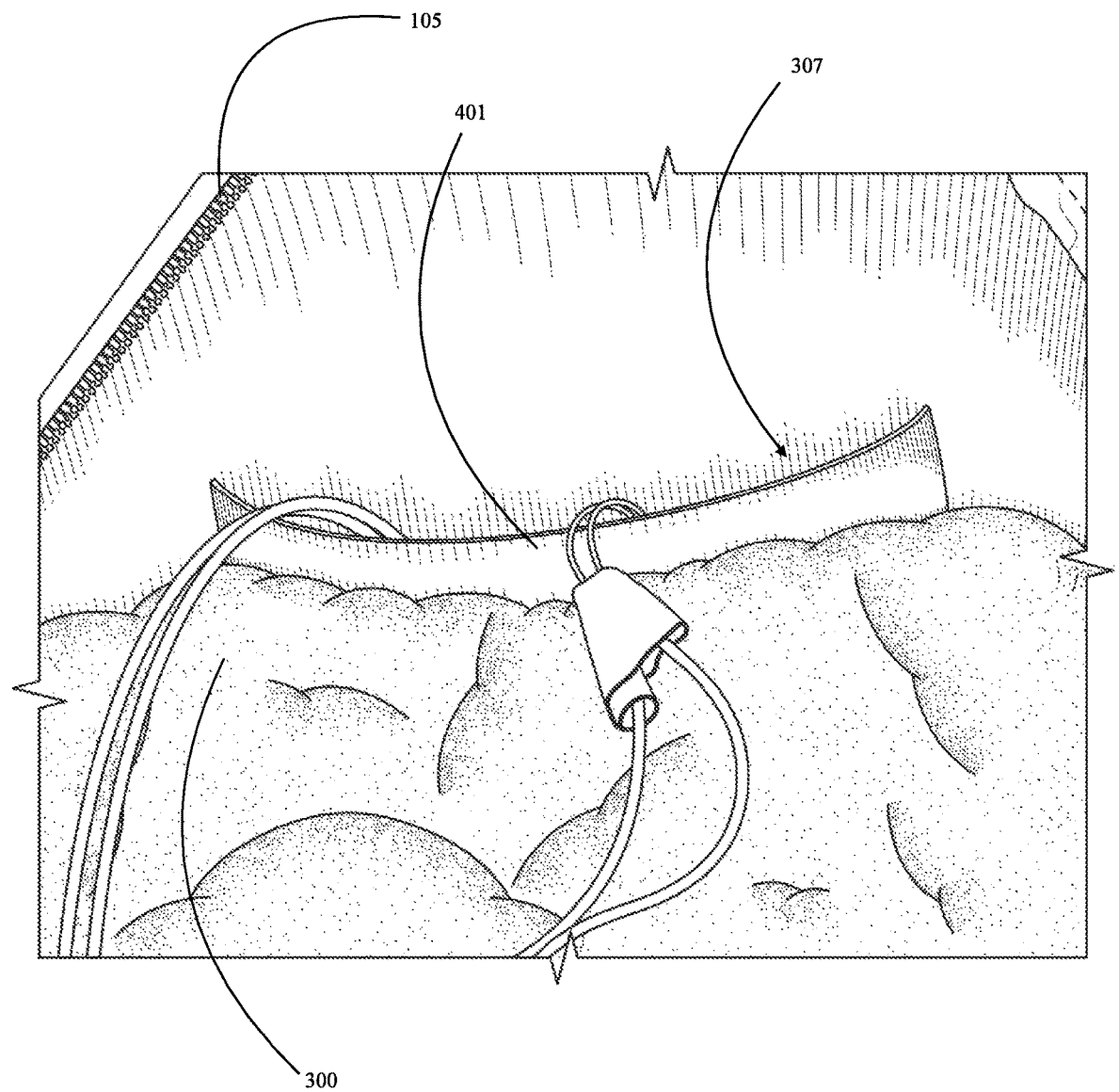
FIG. 4 illustrates a detailed view of the interior cavity of the device and relative positioning of electronic components within the secondary interior pocket, according to an embodiment of the present invention.

Now referring to FIG. 3, a detailed view of the interior cavity 103 of the system 100 is shown in an embodiment of the present invention. Batting 300 or other means of cushion and body support may be disposed within the interior cavity to promote comfort during use of the device. An interior surface 305 defines an interior wall of the system 100 which opposes the exterior surface 101. A secondary pocket 303 is positioned between the batting 300 and interior surface 305. The secondary pocket 303 is configured to retain electrical components comprising the electrical component assembly 500 within the secondary pocket interior 307 of the interior cavity 103. Shown in FIG. 4 is the secondary pocket exterior surface 401 of the secondary pocket 303, in contact with the batting 300 of the system 100. To ensure proper conduction to the skeletal framework of the user, the electrical components, and specifically the bone conduction transducers 509, 511 directly contact the interior surface 305 of the device interior cavity 103.

In another embodiment, the secondary pocket 303 may be removably engaged with the interior of the system 100 permitting the user to selectively dispose the electrical components 500 therein.

Suitable application positions of the transducers include bodily regions such as the cranium, spine, hip, or leg bones. One skilled in the arts may appreciate that any point along the skeletal framework of the user may be effective in conducting sound waves to the user's vestibular and/or somatosensory systems. To permit modulation of the position of the transducers 509, 511, the secondary pocket 303 may be removably engaged with the interior surface 305 of the device interior cavity 103 of the system 100.

In another embodiment, the one or more bone conduction transducers 509, 511 are utilized to provide sound wave bone conduction in frequencies primarily between 50 and 4,000 Hertz ("Hz").

In another embodiment, cushioned transducer interfaces 515 may be made in differing sizes and thicknesses to permit the transducer 509, 511 to be used in a variety of body support device configurations not limited to pillows. Alternative embodiments of body support device 100 may include bedding, massage tables and chairs as well as other commercially and privately used support devices.

Figure 5:
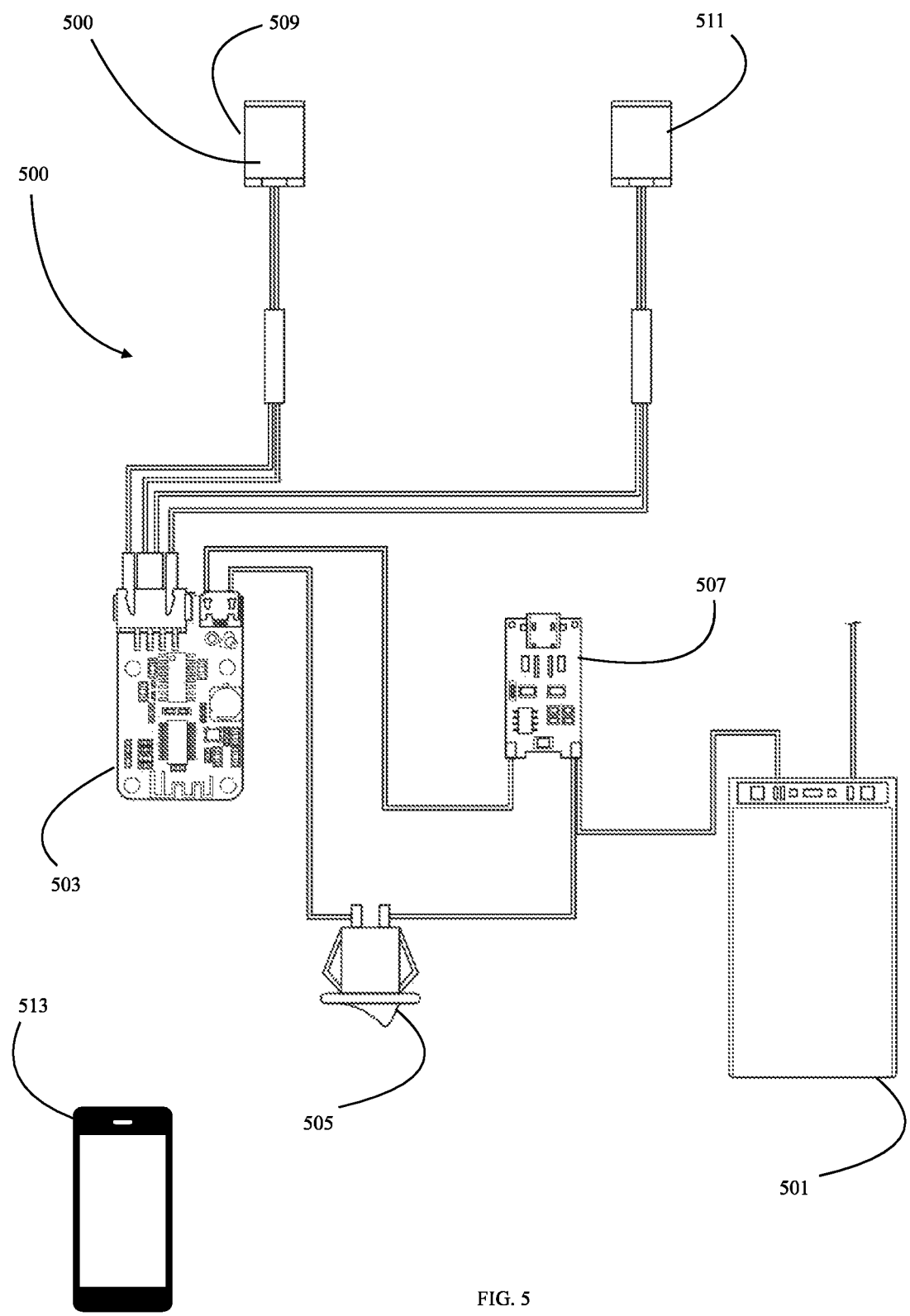
FIG. 5 illustrates a schematic of the electrical components, according to an embodiment of the present invention.
Figure 6:
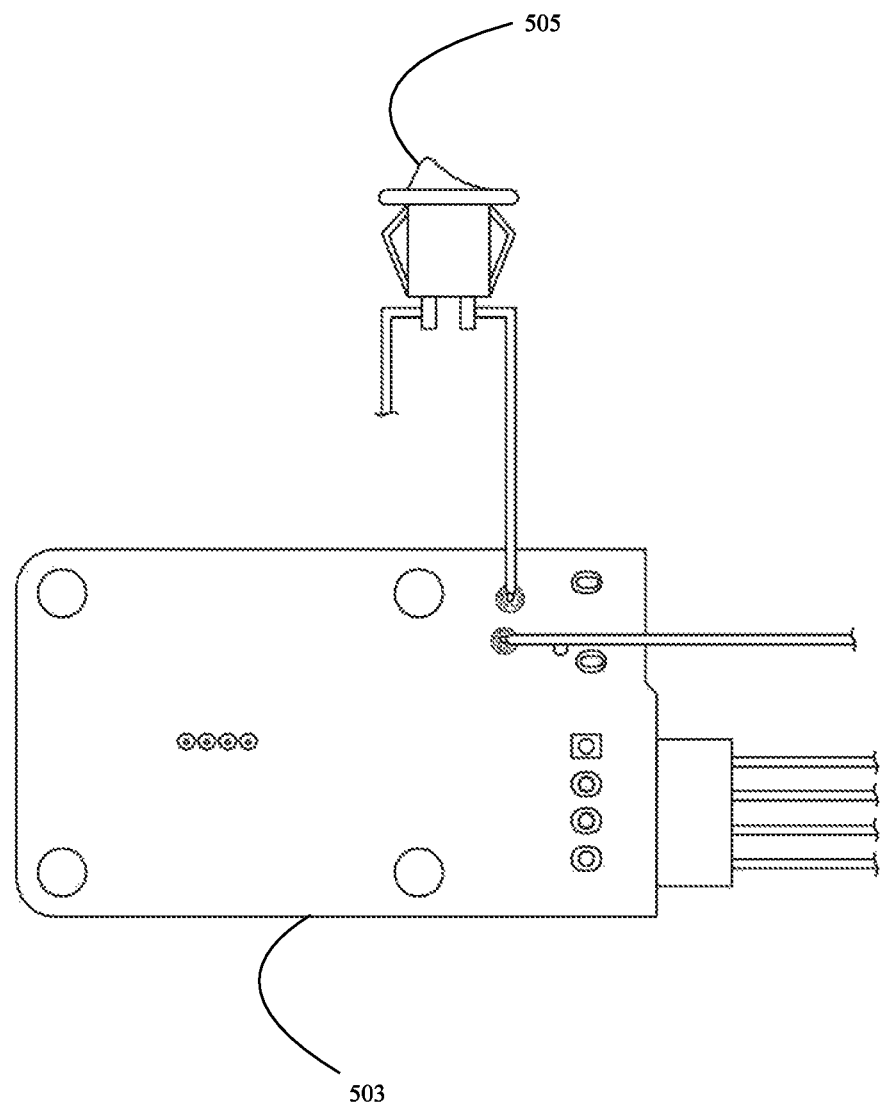
FIG. 6 illustrates a detailed view of the ON/OFF and receiver components, according to an embodiment of the present invention.
Figure 7:
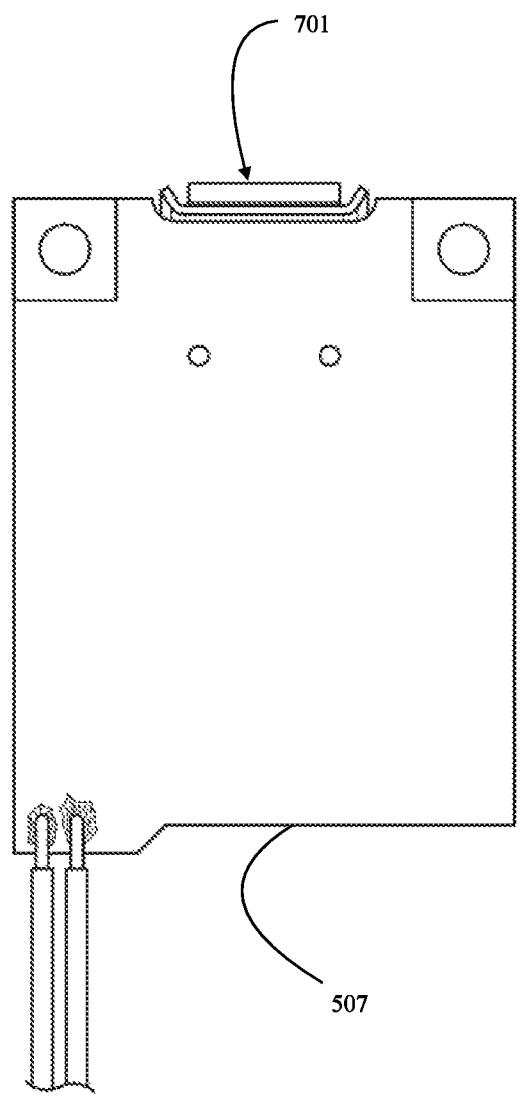
FIG. 7 illustrates a detailed view of the USB component, according to an embodiment of the present invention.

In reference to FIGS. 5-7, the body support device may be comprised of one or more wireless transmitter chips such as a wireless transmitter/receiver 503, an ON/OFF switch 505, one or more power storage means such as battery 501, and a Universal Serial Bus (USB) 507 implement. The USB may be a USB-C component allowing for reception and transmission of data as well as electrical energy to and from the battery 501. The wireless transmitter 503 chip may include any means for wireless transmission of data over short or long distances such as Bluetooth.

The ON/OFF switch 505 may be disposed within the interior cavity 103 or positioned through the exterior surface 101 permitting the user to switch from ON to OFF without opening the interior cavity 103. Further, the ON/OFF switch 505 may be engaged and disengaged using the wireless transmitter 503.

The instant embodiment illustrates a pair of bone conduction transducers 509, 511 which may be positioned anywhere within the interior cavity 103 to engage any points on the user's body where the vestibular/somatosensory systems may be stimulated. It may be preferential for each transducer 509, 511 to be placed on each temple of the user.

In order for sound to be transmitted through the plurality of transducers, a recording playback device 513 is in communication with the system 100. Sound sources may include CD players, MP3 players, tape players, or other sources of sound well known in the arts. Further, the Bluetooth chip 503 embedded within the device may permit any device having wireless connectivity capabilities to be utilized including portable and static computer systems, PDA's, tablets, and mobile phones to be utilized in the transmission of sound to the device.

For example, an amplifier (in the device having wireless connectivity capabilities 503) operates in response to user input that controls the application of music tonal frequencies to the amplifier n communication with the bone conduction transducers 509, 511. This can be achieved by using a hard-wired control, or a wireless control. The wireless control can use RF signals, IR signals, etc. Control supplies the source of music, and controls the application of the source of music to the amplifier and bone conduction transducers 509, 511.

Sounds selected for transmission may include any embodiment typically utilized in the arts including full-spectrum music, low frequency sound, predetermined frequency filtered sounds, recordings of physiological and anatomical sounds among other rhythmic or otherwise therapeutic sounds having the desired neurological, physiological, or other stimulatory effects.

Figure 8:
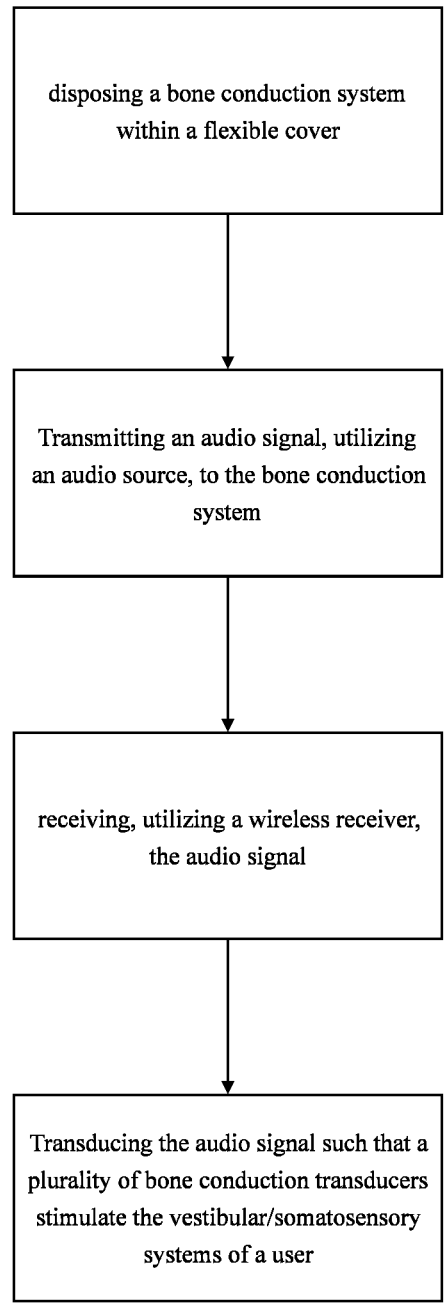
FIG. 8 illustrates a flowchart of a method of stimulating the vestibular/somatosensory systems of a user.

FIG. 8 illustrates a flowchart of a method for stimulating the vestibular/cochlear systems of a user. In step 10 the bone conduction system 100 is disposed within a flexible cover. In step 20 an audio signal is transmitted from an audio source 513 to the bone conduction system. In step 30 the signal is then received by the wireless receiver 503. And finally, in step 40, the signal is transduced by the plurality of bone conduction transducers 509, 511 to stimulate the user.

Power storage means such as a battery are configured to send and receive power throughout the electrical components 500.

In an embodiment, amplitude adjustment to the bone conduction output signal from the amplifier is transmitted through multi conductor bone conduction output jack 701 to a multi-conductor bone conduction output plug that is connected to a bone conduction transducer 509, 511 contained in a pillow. The bone conduction transducer 509, 511 is located within pillow assembly so that when the pillow assembly is supporting the user the bone conduction transducer is in contact with the subject's skeletal frame.

In an embodiment, the filtered and treated audio data are loaded onto a recording playback device, such as an iPod™ device or similar electronic data storage implement. In this embodiment, a wireless connection between the treated audio data stored on the recording playback device and a plurality of bone conduction devices permit a group of individuals to share the same bone conduction signal in a group setting, or likewise in a solitary setting.

One skilled in the art may appreciate that both mono and stereo audio configurations may be utilized depending on the type of audio broadcast. A stereo configuration may be preferable if a plurality of bone conduction transducers are used as well as the intended effect; whether for auditory pleasure or therapy.

In another embodiment, a signal from the recording playback device 513 is provided to an input of an amplifier/splitter where it is split into a bone conduction output signal which is connected to one or more bone conduction transducers. The amplifier provides for adjustment of the amplitude of the bone conduction output signal. The bone conduction output signal can thus be broadcast for all users in communication with the community of bone conduction transducers in the bone conduction system 100 via the wireless system if desired.

Each transducer system may include the transducer that is coupled to a diaphragm 519. Each diaphragm 519 can be made from a light, thin plastic material or composite such as a carbon fiber/Kevlar composite material. Plastics can include polycarbonate, polypropylene, polyethylene, or any other desired plastic material that is capable of transmitting the tonal frequencies of music through the diaphragm 519. Elongated members may allow the diaphragm 519 to react to lower frequency inputs by the transducer. The elongated members also allow for flexibility of the diaphragm 519 which further increases the transfer of vibrational tonal frequencies into the medium in which the diaphragm 519 is connected. Preferentially, each diaphragm 519 is in sufficient contact with the skeletal framework of the user. A preferential contact point may include human temporal bones.

In another embodiment, the bone conduction output signal is transmitted to a wireless transmitter for transmission to associated wireless receivers. A wireless signal is thus communicated from wireless transmitter to a plurality of wireless receivers, one associated with each set of bone conduction body support devices. Each wireless receiver comprises a separate amplifier to boost the signal strength for adjusting the volume of the bone conduction transducers. Bone conduction transducers are similar to the transducer assembly 509 or 511 shown in FIG. 5.

In alternative embodiments, the body support systems 100 may also comprise a heater (not shown) with a control (not shown) regulate the temperature of the pad. In another embodiment, the exterior flexible sheet of padding 112 may comprise locations (not shown) for aromatherapy material for depositing a plurality of fragrances and/or a plurality of light emitting devices for light therapy.

Further, embodiments may include both air conduction and bone conduction integrations into the systems 100.

Another type of transducer that can be used to transmit music and tones to the surface of the body is an electro-active polymers (EAPs). EAPs are disclosed in an article entitled "Artificial Muscles" by Steven Ashley, *Scientific American*, October 2003, pp. 53-59. Electro-active polymers are polymers that move in response to an electrical current. As disclosed in the *Scientific American* article, supra, "The fundamental mechanism underlying new artificial muscle products relatively simple. When exposed to high-voltage electric fields, dielectric elastomers—such as silicones and acrylics—contract in the direction of the electric field lines and expand perpendicularly to them, a phenomenon physicists term Maxwell stress.

The exterior surface of the body support device may be constructed of any fabric known in the textile arts commonly associated with pillows. This may include cotton, polyester, silk, or blends of any commonly utilized materials.

Meanwhile, the interior cushion (e.g. the batting or filling) may be comprised of common materials known in the arts such as latex, polyester, feather, viscoelastic memory foam, down and gel as well as blends of any common materials.

In another embodiment, the bone conduction system 100 is configured as a seat, such as an automobile seat. In yet another embodiment, the bone conduction system 100 is configured as a hospital bed cushion as a component of a means for therapeutic treatment.

It will be appreciated by persons skilled in the art that the present embodiment is not limited to what has been particularly shown and described hereinabove. A variety of modifications and variations are possible in light of the above teachings without departing from the following claims.

What is claimed is:

1. A bone conduction device comprising;
a flexible cover having an exterior surface and an interior cavity comprising a plurality of removably engageable secondary pockets therein, the flexible cover having batting disposed therein;
a plurality of repositionable bone conduction transducers, each of the bone conduction transducers in the plurality of bone conduction transducers disposed within a respective one of the plurality of removably engagable secondary pockets, the plurality of bone conduction transducers disposed between the flexible cover and the batting, wherein each of the plurality of bone conduction transducers are configured to transmit sounds waves to stimulate a user through bone conduction;
a sound source in communication with a wireless transmitter, wherein the wireless transmitter is electrically connected to and transmitting signals to the plurality of bone conduction transducers; and
one or more USB ports electrically connected to a power source, wherein the power source is configured to receive, store, and transmit power to the plurality of bone conduction transducers.

2. The device of claim 1, further comprising a control panel disposed on the exterior surface of the flexible cover permitting the user to manage audio levels, ON/OFF functions, and other functions of the device from the exterior surface of the flexible cover.

3. The device of claim 1 wherein each of the bone conduction transducers in the plurality of bone conduction transducers is positioned proximate to a head of the user.

4. The device of claim 3, wherein each of the bone conduction transducers in the plurality of bone conduction transducers is proximately positioned to contact a temporal bone of the user.

5. The device of claim 1 wherein each of the bone conduction transducers in the plurality of bone conduction transducers is configured to emit sound vibrations having a frequency range between 50 and 4,000 Hz.

6. The device of claim 1 wherein the flexible cover is made of a textile.

7. The device of claim 1 wherein the batting disposed within the flexible cover is configured to support at least one human body part.

8. The device of claim 1 wherein the wireless transmitter, the one or more USB ports, the battery, and the sound source are disposed within the interior cavity.

9. The device of claim 1, wherein the interior cavity is selectively opened utilizing a textile connection means.

10. The device of claim 1 wherein the device is configured as a pillow.

11. The device of claim 1 wherein the device is configured as a seat.

12. The device of claim 1 wherein the device is configured as a bed cushion.

13. A method of stimulating a user using bone conduction comprising the steps of:
    providing a bone conduction system within a flexible cover comprising an interior cavity with a plurality of removably engageable secondary pockets therein for the selective placement of electrical components;
    the bone conduction system comprising a wireless receiver, a plurality of repositionable bone conduction transducers and a control panel, wherein the control panel is disposed on an exterior surface of the flexible cover thereby permitting the user to manage audio levels, ON/OFF functions, and other functions of the system from the exterior of the cover;
    transmitting an audio signal, utilizing an audio source, to the bone conduction system;
    receiving the audio signal utilizing the wireless receiver; and
    transducing the audio signal such that the plurality of bone conduction transducers stimulate a vestibular/somatosensory system of the user.

14. The method of claim 13, wherein the bone conduction system further comprises one or more USB ports.

15. The method of claim 13, wherein the bone conduction system further comprises a battery.

16. The method of claim 13, wherein the flexible cover is configured as a pillow.

17. The method of claim 13, wherein the flexible cover is configured as a seat.

18. The method of claim 13, wherein the flexible cover is configured as a bed cushion.

19. The method of claim 13, wherein the interior cavity of the flexible cover may be is selectively opened utilizing a textile connection means.

* * * * *